US00PP36438P2

(12) United States Plant Patent
Erhart

(10) Patent No.: US PP36,438 P2
(45) Date of Patent: Feb. 11, 2025

(54) ***HIBISCUS* PLANT NAMED 'WALHIFLAR'**

(50) Latin Name: ***Hibiscus paramutabilis* x *syriacus***
Varietal Denomination: WALHIFLAR

(71) Applicant: Walberton Plants Limited, Walberton (GB)

(72) Inventor: Eva Erhart, Walberton (GB)

(73) Assignee: Wallburton Plants Limited (GB)

( * ) Notice: Subject to any disclaimer, the term of this patent is extended or adjusted under 35 U.S.C. 154(b) by 0 days.

(21) Appl. No.: 18/670,965

(22) Filed: May 22, 2024

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
CPC . A01H 5/02; A01H 5/00; A01H 6/608; A01H 6/60
See application file for complete search history.

(56) References Cited

U.S. PATENT DOCUMENTS

PP24,936 P2 * 9/2014 Tristram ..... A01H 6/608 Plt./257
PP29,683 P3 * 9/2018 Woods ..... Plt./257

OTHER PUBLICATIONS

BBC Gardeners World Live 2023 Hot Off the Potting Bench, retrieved on Aug. 22, 2024 at https://www.bbcgardenersworldlive.com/wp-content/uploads/2023/06/New-Plant-list-for-GWL-LT-1.pdf, 11 pp. (Year: 2023).*

CPVO Community Plant Variety Office Version 4.20.5, retrieved on Aug. 22, 2024 at https://online.plantvarieties.eu/publicConsultationDetails?registerId=20241014&denomination=walhiflar, 2 pp. (Year: 2024).*

Hort News Hot off the Potting Bench at BBC Gardeners World live 2023, retrieved on Aug. 22, 2024 at https://hortnews.com/hot-off-the-potting-bench-at-bbc-gardeners-world-live/, 3 pp. (Year: 2023).*

* cited by examiner

*Primary Examiner* — June Hwu
(74) *Attorney, Agent, or Firm* — Cassandra Bright

(57) ABSTRACT

A new and distinct cultivar of *Hibiscus* plant named 'WALHIFLAR' is disclosed, characterized by large, white flowers with a large, deep red eye. Plants are observed winter-hardy to −10 degrees Celsius and heat tolerant to 40 Celsius without adverse effect. Growth habit is broadly upright and spreading more with age. The new variety is a *Hibiscus*, typically produced as an outdoor ornamental plant.

2 Drawing Sheets

Latin name of the genus and species: *Hibiscus paramutabilis* x *syriacus*.

Variety denomination: 'WALHIFLAR'.

BACKGROUND OF THE INVENTION

The new *Hibiscus* cultivar is a product of a planned breeding program by the inventor. *Hibiscus* 'WALHIFLAR' is the result of the crossing of the seed parent, *Hibiscus* '99S92', an unpatented proprietary seedling from the breeder's own program, and the pollen parent, an unidentified *Hibiscus* variety. The crossing resulting in this new variety was made during 2015 at a nursery in Walberton, United Kingdom.

The new cultivar was found and selected by the inventor in a group of seedlings at the same nursery in Walberton, United Kingdom during 2016.

Asexual reproduction of the new cultivar 'WALHIFLAR' was first performed in July of 2019 in Walberton, United Kingdom, by softwood cuttings. Subsequent propagation has shown that the unique features of this cultivar are stable and reproduced true to type in successive generations.

SUMMARY OF THE INVENTION

The cultivar 'WALHIFLAR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'WALHIFLAR'. These characteristics in combination distinguish 'WALHIFLAR' as a new and distinct *Hibiscus* cultivar:

1. Large white flowers with a dark red eye.
2. Broadly upright habit.
3. Winter hardiness to at least −10° C.

PARENT COMPARISONS

Details of the parent varieties are not available for comparisons.

COMMERCIAL COMPARISONS

Plants of 'WALHIFLAR' are similar in some horticultural characteristics to the variety *Hibiscus* 'RWOODS5', U.S. Plant Pat. No. 29,683. The new variety, however, differs in the following:

1. Flowers of the new variety are single, while flowers of this comparator are semi-double.
2. Flowers of the new variety are larger than flowers of this comparator.

Plants of 'WALHIFLAR' are similar in some horticultural characteristics to the variety *Hibiscus* 'Red Heart', unpatented. The new variety, however, differs in the following:

1. Flowers of the new variety are much smaller than flowers of this comparator.
2. Flowers of the new variety have a larger eye than flowers of this comparator.

Plants of 'WALHIFLAR' are similar in some horticultural characteristics to the variety *Hibiscus* 'Hamabo', unpatented. The new variety, however, differs in the following:

1. Flowers of the new variety are much larger than flowers of this comparator.

Plants of 'WALHIFLAR' are similar in some horticultural characteristics to the variety *Hibiscus* 'WALHIROSMO', U.S. Plant Pat. No. 24,936. The new variety, however, differs in the following:

1. Petals of the new variety strongly overlap, while petals of this comparator do not overlap or overlap very weakly.

BRIEF DESCRIPTION OF THE PHOTOGRAPHS

Figure 1:
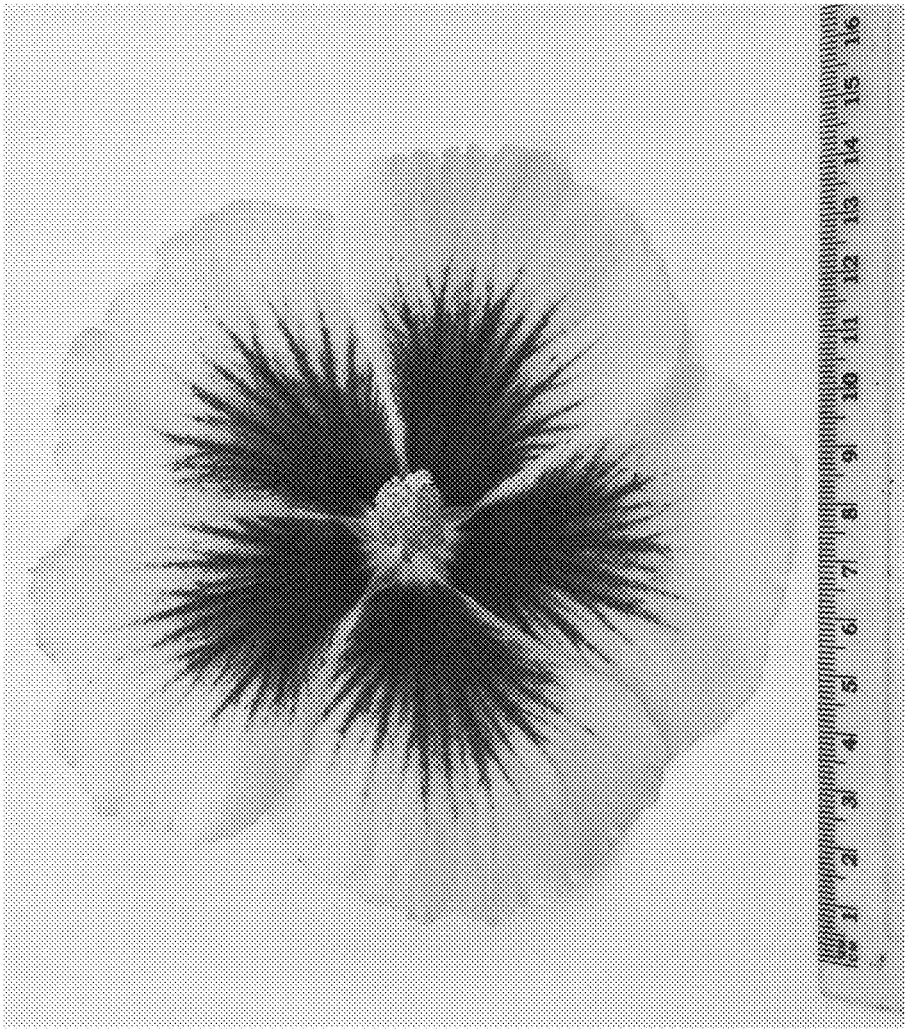

The accompanying drawing, FIG. 1 illustrates in full color a typical flower from a typical plant of 'WALHIFLAR' grown in an unheated glasshouse at a nursery in Walberton, United Kingdom. This plant producing this flower is approximately 3 years old.

Figure 2:
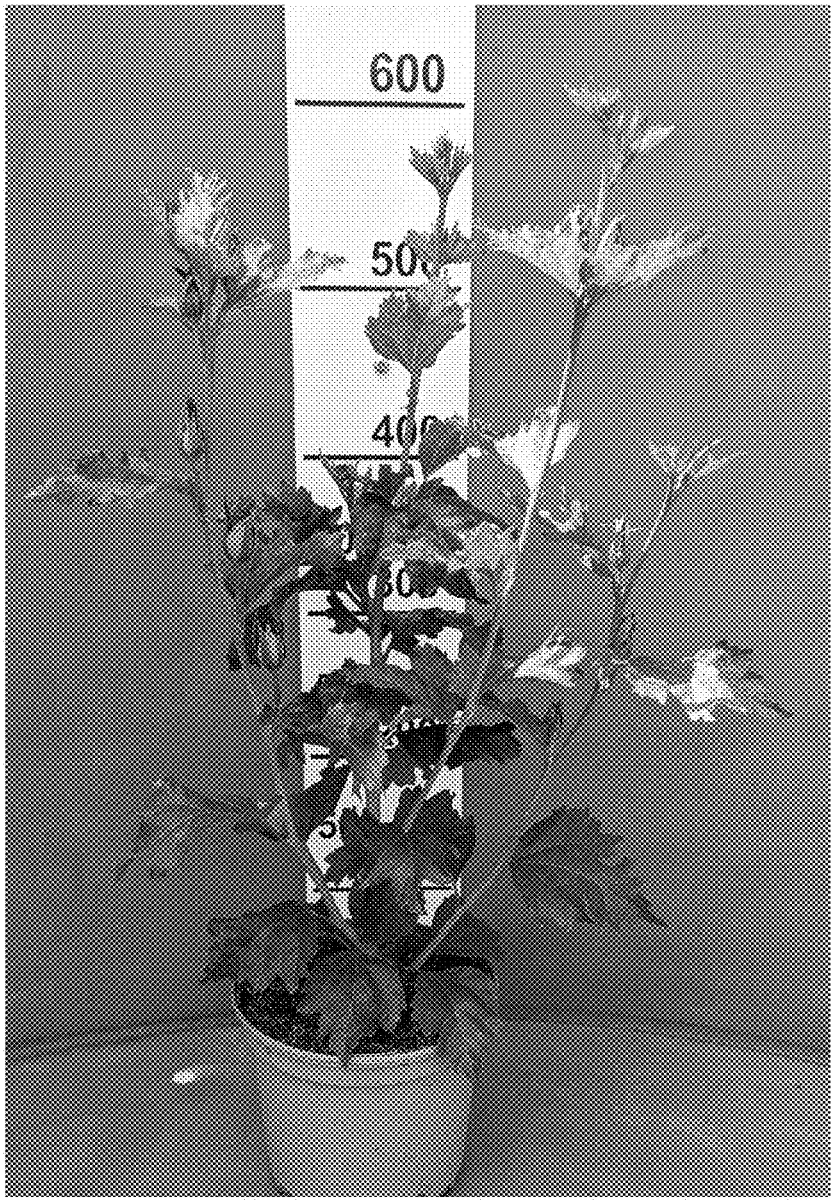

FIG. 2 illustrates a plant of about 1-year old during May, just before flowering begins.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe a 'WALHIFLAR' plant. This plant is approximately 3 years old, shown in a 6 liter container. Temperatures ranged from 0° C. to 33° C. during the day to −8° C. to 18° C. at night. No artificial light, photoperiodic treatments were given to the plants. Measurements and numerical values represent averages of typical plant types.

Botanical classification: *Hibiscus paramutabilis* x *syriacus* 'WALHIFLAR'.

PROPAGATION

Time to initiate roots: 20 to 24 days in summer; 14 to 18 weeks in winter at 0° C. to 33° C.

Root description: Fine, fibrous.

PLANT

Plant type: Deciduous flowering shrub.

Age of plant described: 3 years old.

Growth habit: Broadly upright, spreading slightly with age.

Growth rate: Moderate.

Height: 85 cm.

Plant spread: 110 cm.

Branching characteristics:

Primary lateral branches:

*Quantity*.—Typically 12 to 18.

*Length*.—52 cm.

*Diameter*.—0.65 cm, tapering to 0.3 cm near apex.

*Shape*.—Virgate, upright, compact; outwardly spreading in maturity.

*Strength*.—Stiff, strong.

*Color*.—RHS Yellow-Green N144A and 151A near apex, fading to between 148A and 146B on mature wood.

*Texture*.—Verrucose, sparsely puberulent.

Internode length: 2 to 2.5 cm.

FOLIAGE

Leaf:

*Arrangement*.—Alternate, spirally arranged, dextrorse; leaves held singly, rarely in 2s or 3s at lower (older) nodes.

*Quantity*.—15 to 22 per branch.

*Average length*.—6.6 cm.

*Average width*.—7.1 cm.

*Shape of blade*.—Palmatifid, three-lobed. Medium lobing.

*Apex*.—Acute.

*Base*.—Subcordate to hastate.

*Margin*.—Medium serrate, teeth 0.2 to 0.3 cm deep.

*Texture of top surface*.—Areolate, sparsely hispid.

*Texture of bottom surface*.—Areolate, moderately to sparsely hispid.

*Aspect*.—Petiole held 30° to 40° from stem.

*Leaf undulation*.—Weak.

*Color*.—Young foliage upper side: RHS Yellow-Green 144A. Young foliage under side: RHS Yellow-Green 144A flushed 144B. Mature foliage upper side: RHS Yellow-Green 147A. Mature foliage under side: RHS Yellow-Green 147B. Autumn color upper side: RHS Yellow-Orange 16B. Autumn color under side: RHS Yellow-Orange 16B.

*Venation*.—Type: Palmate. Venation color, upper side: RHS Yellow-Green 147B. Venation color, under side: RHS Yellow-Green 147C.

*Petiole*.—Length: 1.1 cm. Diameter: 0.2 cm. Color: RHS Yellow-Green 147B. Texture: Moderately tomentose.

FLOWER

Natural flowering season: May to September in Walberton, UK.

Flower type and habit: Single, rotate, overlapping.

Rate of flower opening: 2 to 3 days from bud dehiscence (cracking color) to fully opened flower.

Flower longevity on plant: 2 to 3 days.

Persistence: Self-cleaning.

Fragrance: None.

Bud:

*Shape*.—Ovate.

*Length*.—2.4 cm.

*Diameter*.—1.6 cm at widest.

*Apex*.—Acute to attenuate.

*Base*.—Rounded.

*Texture*.—Scabrid to verrucose.
*Color*.—RHS Yellow-Green 146D.

Flower size:
*Diameter*.—12.4 cm.
*Depth*.—4.5 cm.

Petals:
*Quantity*.—5.
*Arrangement*.—Rotate.
*Length*.—6.2 cm.
*Width*.—6.7 cm at widest.
*Shape*.—Orbicular to obovate.
*Apex*.—Rounded.
*Base*.—Obtuse.
*Margin*.—Entire to slightly serrate at the sides; slightly and irregularly crenate, undulate at the outer edges.
*Texture, upper and lower surfaces*.—Glabrous, slightly shiny.
*Petal undulation*.—Weak.
*Color*.—Eye — size and feathering: Extends 55% to 60% of length of petal from petal base, moderate feathering. When opening, upper surface, main color: Near RHS White N155B. When opening, upper surface, eye color: RHS Greyed-Purple 187A and 187B at center and on veins, fading to Red-Purple 59C and Red-Purple 61A at feathering, and fading further to Red-Purple 64A at outermost feathering. When opening, lower surface: Near RHS White N155D, veins close to N155A. Fully opened, upper surface, main color: Near RHS White N155B. Fully opened, upper surface, eye color: RHS Greyed-Purple 187B, fading to Red-Purple 59C at feathering, fading further to 64B at outermost feathering. Fully opened, lower surface: Near RHS White NN155D, veins close to N155A.

Calyx sepals:
*Quantity*.—5.
*Length*.—2.3 to 2.6 cm.
*Width*.—1 to 1.1 cm at widest part.
*Shape* (*overall*).—Broadly ovate to lanceolate, campanulate. Apex: Acute to attenuate. Base: Truncate, fused.
*Margin*.—Entire.
*Color*.—Upper and lower surfaces Near RHS Yellow-Green N148A and N148B, colors mixed.
*Texture*.—Strigose to scabrid.

Epicalyx sepals:
*Quantity*.—5 to 7, typically 6.
*Length*.—2.3 cm.
*Width*.—0.3 cm at widest part.
*Shape* (*overall*).—Linear-lanceolate, fused at base; campanulate overall.
*Apex*.—Acute.
*Base*.—Truncate.
*Margin*.—Entire.
*Color*.—Upper and lower surfaces RHS Yellow-Green 148B.
*Texture*.—Strigose to scabrid.

Peduncle:
*Length*.—1.7 cm.
*Diameter*.—0.3 cm.
*Angle*.—45° to the lateral branch.
*Strength*.—Strong, rigid.
*Texture*.—Scabrid to strigose.
*Color*.—RHS Yellow-Green N148A.

REPRODUCTIVE ORGANS

Stamen stalk:
*Length*.—2.4 cm.
*Diameter*.—0.4 cm at base, tapering to 0.25 to 0.3 cm near apex.
*Color*.—Between RHS White NN155D and pure white.
*Protruding beyond petals*.—Moderately protruding in fully opened flowers.

Stamens:
*Quantity*.—Typically between 60 and 80.
*Arrangement on stalk*.—6 to 8 whorls.

Anthers:
*Shape*.—Globular.
*Length*.—Approximately 0.1 to 0.2 cm.
*Color*.—RHS Greyed-Yellow 158B.
*Pollen*.—Color: RHS Yellow 12C. Quantity: Sparse.

Pistil:
*Number*.—5.
*Length*.—0.4 cm.
*Style*.—Length: 0.3 cm. Color: Near RHS White N155D.
*Stigma*.—Shape: Oblately globular. Color: RHS White 155B. Ovary Color: RHS Yellow-Green 150D and 154D, both colors present.

OTHER CHARACTERISTICS

Seeds: Not observed.

Disease/pest resistance: Neither resistance nor susceptibility to normal diseases and pests of *Hibiscus paramutabilis* x *Hibiscus syriacus* have been observed.

Temperature tolerance: Trialed without adverse effect at temperatures ranging between −10° C. to 40° C.

What is claimed is:

1. A new and distinct cultivar of *Hibiscus* plant named 'WALHIFLAR' as herein illustrated and described.

* * * * *